United States Patent
Shah et al.

(10) Patent No.: US 10,485,745 B2
(45) Date of Patent: Nov. 26, 2019

(54) UV-A/UV-B SUNSCREEN COMPOSITION

(71) Applicant: L'OREAL, Paris (FR)

(72) Inventors: Anil Shah, East Windsor, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 91 days.

(21) Appl. No.: 15/142,929

(22) Filed: Apr. 29, 2016

(65) Prior Publication Data

US 2017/0312199 A1 Nov. 2, 2017

(51) Int. Cl.
| | | |
|---|---|---|
| *A61Q 17/04* | (2006.01) | |
| *A61K 8/81* | (2006.01) | |
| *A61K 8/37* | (2006.01) | |
| *A61K 8/06* | (2006.01) | |
| *A61K 8/35* | (2006.01) | |
| *A61K 8/02* | (2006.01) | |
| *A61K 8/40* | (2006.01) | |

(52) U.S. Cl.
CPC .............. *A61K 8/37* (2013.01); *A61K 8/0279* (2013.01); *A61K 8/062* (2013.01); *A61K 8/064* (2013.01); *A61K 8/35* (2013.01); *A61K 8/40* (2013.01); *A61K 8/8147* (2013.01); *A61Q 17/04* (2013.01); *A61K 2800/26* (2013.01); *A61K 2800/262* (2013.01); *A61K 2800/30* (2013.01); *A61K 2800/52* (2013.01); *A61K 2800/522* (2013.01); *A61K 2800/60* (2013.01)

(58) Field of Classification Search
None
See application file for complete search history.

(56) References Cited

U.S. PATENT DOCUMENTS

| | | |
|---|---|---|
| 5,116,604 A | 5/1992 | Fogel et al. |
| 5,476,648 A | 12/1995 | Fogel |
| 5,505,948 A | 4/1996 | Rapaport |
| 5,620,682 A | 4/1997 | Fogel |
| 5,624,663 A | 4/1997 | Deflandre et al. |
| 6,210,658 B1 | 4/2001 | Bonda |
| 8,557,227 B2 | 10/2013 | Simonnet et al. |
| 9,050,475 B2 | 6/2015 | Nurse et al. |
| 2004/0247536 A1 | 12/2004 | Chaudhuri |
| 2009/0009807 A1 | 1/2009 | Sugi |
| 2012/0015016 A1 | 1/2012 | Galdi et al. |
| 2013/0028853 A1 * | 1/2013 | Nurse ...................... A61K 8/35 424/60 |
| 2013/0078200 A1 | 3/2013 | Daly et al. |
| 2013/0101515 A1 * | 4/2013 | Meyer ...................... A61K 8/37 424/9.2 |
| 2013/0129650 A1 | 5/2013 | Simonnet et al. |
| 2014/0170090 A1 | 6/2014 | Thaggard |
| 2015/0202139 A1 | 7/2015 | Friedman |

FOREIGN PATENT DOCUMENTS

| | | | |
|---|---|---|---|
| EP | 0796077 B1 | 6/2002 | |
| EP | 2874710 A2 | 5/2015 | |
| WO | 2014012699 A2 | 1/2014 | |
| WO | WO-2014114888 A2 * | 7/2014 | ............. A61K 8/375 |
| WO | WO-2014140312 A1 * | 9/2014 | ............. A61K 36/87 |
| WO | 2014165490 A2 | 10/2014 | |
| WO | 2015118038 A1 | 8/2015 | |
| WO | 2015124233 A1 | 8/2015 | |
| WO | WO-2015126874 A1 * | 8/2015 | ............. A61Q 17/04 |
| WO | WO-2017053959 A1 * | 3/2017 | ........... A61K 8/8182 |

OTHER PUBLICATIONS

Xue "The Secret World of SPF Enhancers," Aug. 14, 2014; http://www.byrdie.com/spf-enhancers.*
Dow "SUNSPHERES," Feb. 2006; http://www.dow.com/assets/attachments/business/pcare/sunspheres/sunspheres_powder/tds/sunspheres_powder.pdf.*
Machine translation WO 2014/114888, printed 2017.*
Prospector "Oxynex® ST liquid," printed 2017; https://www.ulprospector.com/en/asia/PersonalCare/Detail/1193/51545/Oxynex-ST-Liquid.*
Oresajo et al. "Complementary effects of antioxidants and sunscreens in reducing UV-induced skin damage as demonstrated by skin biomarker expression," Journal of Cosmetic and Laser Therapy 12:157-162, 2010.*
Elton et al. "Application of styrene/acrylates copolymer (SunSpheres) in cosmetic systems," Research Disclosure 428009, Dec. 1999.*
International Search Report dated Jun. 22, 2017 for PCT/US2017/028348.

* cited by examiner

*Primary Examiner* — David J Blanchard
*Assistant Examiner* — Alissa Prosser
(74) *Attorney, Agent, or Firm* — McNees Wallace & Nurick LLC

(57) ABSTRACT

A photostable UV-A/UV-B-sunscreen composition is provided. The composition includes an oil in water or water in oil emulsion, wherein the emulsion includes at least one photostabilizer having anti-oxidant properties, at least one SPF booster, and at least one UV-A filter and at least one UV-B filter. The UV-A/UV-B sunscreen composition is provided in which the composition is essentially free of oxybenzone.

2 Claims, No Drawings

UV-A/UV-B SUNSCREEN COMPOSITION

FIELD OF THE INVENTION

The present invention is directed to photostable UV-A/UV-B sunscreen compositions, More specifically, the present invention is directed to a UV-A/UV-B sunscreen composition having no oxybenzone.

BACKGROUND OF THE INVENTION

The photoprotection of keratinous substrates, including both skin and hair, is considered by many to be necessary in order to facilitate protection from sun-damage, sunburn, photo-aging, as well as to decrease the chances of skin cancer development caused by exposure to ultraviolet ("UV") radiation. There are typically two types of UV-A/UV-B sunscreen compositions used to accomplish photoprotection, namely, inorganic UV filters and organic UV filters.

Inorganic UV filters such as titanium dioxide and zinc oxide are typically employed in large quantities in order to ensure proper coverage/maximum protection over the surface onto which they are applied. As a result, inorganic UV filters have a tendency to cause skin to which they are applied to feel dry, and further impart an undesirable color onto the treated surface (naturally white, but sometimes colored for aesthetic purposes with varying degrees of aesthetic success).

Further, UV filters may either protect against UV-A radiation (long-wave), UV-B radiation (shortwave), or both. In the past, it was commonly held that protection against UV-B radiation was the primary or even sole consideration in sun-protection. However, more recent research has revealed that exposure to UV-A radiation may also be dangerous and lead to undesirable effects. As such, the current trend in sun-protection endeavors is typically to protect against both UV-A and UV-B in a single composition, and to increase both the SPF and the UV-A ratings of the composition.

Sunscreens are treated as over-the-counter ("OTC") products in many jurisdictions, including in the United States of America ("U.S."), As a result of the classification of sunscreens as OTC products, in the U.S., sunscreen is regulated by the U.S. Food and Drug Administration ("FDA"), which, due to regulatory issues and safety concerns, has limited the active ingredients of sunscreen compositions, such as UV filters, substantially. Thus, there are limited. UV filters available to achieve high efficacy with respect to both SPF and UV-A protection. Most commonly, these UV filters are regarded to include avobenzone, oxybenzone, octisalate, octocrylene, and homosalate.

U.S. Pat. No. 9,050,475 B2 (the '475 patent) discloses methods and compositions for the protection of an object from UV light, which includes multiple photostabilizers but which is essentially free of oxybenzone and oxtinoxate. The '475 patent claims to enhance the SPF by adding antioxidants, photostabilizers and/or film forms. However, the '475 patent does not claim any defined level of UV-A protection. In particular, the '475 patent describes the photostabilization of avobenzone, which is a UV-A filter and which is not itself photostable, however it is not believed that the stabilization of avobenzone, by itself, is capable of enabling a sufficiently high UV-A protection in a composition for current consumer and health requirements and desires.

It is therefore an object of the present invention to provide a composition capable of not only of a defined high SPF rating, but also providing a defined high UV-A rating which has eliminated oxybenzone content.

BRIEF DESCRIPTION OF THE INVENTION

In an exemplary embodiment, a photostable UV-A/UV-B sunscreen composition is disclosed including an oil in water or water in oil emulsion, the emulsion including at least one photostabilizer having anti-oxidant properties, at least one SPF booster, at least one UV-B and at least one UV-A filter. The composition is free of oxybenzone.

In another exemplary embodiment, a photostable UV-A/UV-B sunscreen composition is disclosed including at least one photostabilizer having anti-oxidant properties, at least one SPF booster, and a UV-filter system consisting essentially of avobenzone, octosalate, octocrylene and homosalate. The composition is free of oxybenzone.

Other features and advantages of the present invention will be apparent from the following more detailed description of the preferred embodiment which illustrates, by way of example, the principles of the invention.

DETAILED DESCRIPTION OF THE INVENTION

It has been surprisingly discovered by the inventors that an unexpected synergetic effect may be achieved by combination of at least one photostabilizer and at least one SPF booster in certain proportions with at least one UV-B and one UV-A filter in an emulsion of a photostable UV-A/UV-B sunscreen composition. This composition may be incorporated into a wide variety of cosmetic products such as skincare products and hair care products, including, but not limited to, sunscreens, skin-tanning products, make-up products, lip balms, skin facial peeling products, moisturizers, anti-aging skincare products, and more.

One advantage of an embodiment of the present disclosure includes the beneficial elimination of oxybenzone from sun protectant compositions which are effective against exposure to both UV-A and UV-B radiation, without detrimental reduction in the efficacy of the sun protectant composition. Exemplary embodiments of such photostable UV-A/UV-B sunscreen composition will be further disclosed below.

All numbers expressing quantities of ingredients and/or reaction conditions are understood as being modified in all instances by the term "about", unless otherwise stated.

All SPF and UV-A ratings are provided on the basis of in-vivo value unless otherwise indicated.

In the present application, the term "keratinous substrate," as used herein, includes but is not limited to skin, hair, and nails.

In the present application, the term "ambient temperature" means a temperature of about 25° C.

In the present application, the term "stable" means the emulsion remains intact without phase separation, color and/or odor change over the stability monitoring period and the water-soluble active ingredients remain solubilized in the water phase without crystallization or precipitation out of the emulsion.

In the present application, the term "SPF booster" refers to a material which increases the UV absorption of another material when the two are intermixed in a composition by refracting UV radiation, thereby increasing the effective path length of the UV radiation through the composition.

The photostable UV-A/UV-B sunscreen composition of the present invention can comprise, consist of, or consist essentially of the essential elements and limitations of the invention described herein, as well as any additional or optional ingredients, components, or limitations described herein or otherwise useful in compositions intended for topical application onto keratinous substrates. In one embodiment, the photostable UV-A/UV-B sunscreen composition includes but is not limited to an oil in water or water in oil emulsion, wherein the emulsion includes at least one photostabilizer having anti-oxidant properties, at least one SPF booster, and at least one UV filter. The UV-A/UV-B sunscreen composition according to embodiments of the present invention is essentially free of oxybenzone. As used herein, "essentially free" indicates that oxybenzone is present only in de minimus amounts as an impurity in other ingredients, and the oxybenzone does not materially affect the properties of the composition. In yet another embodiment, the composition is free of oxybenzone. As used herein, "free" indicates that no reliably measurable oxybenzone is present in the composition.

Photostabilizer

The at least one photostabilizer may include any suitable composition, including, but not limited to, diethylhexyl syringylidenemalonate (formula I).

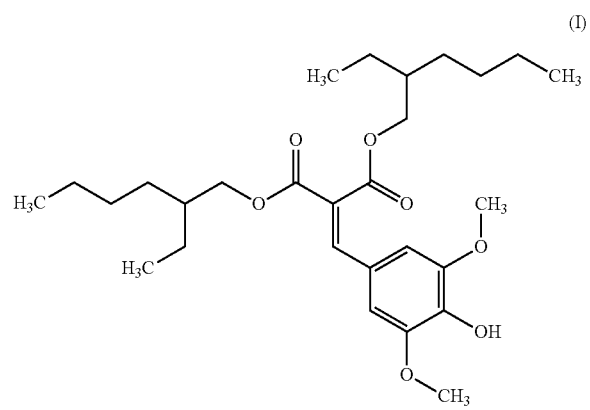 [SMILES: CCCCC(CC)COC(=O)C(=Cc1cc(OC)c(O)c(OC)c1)C(=O)OCC(CC)CCCC]

In one embodiment, the at least one photostabilizer consists of diethylhexyl syringylidenemalonate. Without being bound by theory, it is believed that the photostabilizer may reduce degradation of other materials in the composition due to UV radiation.

SPF Booster

The at least one SPF booster may include any suitable material, including, but not limited to a plurality of light refracting bodies. The plurality of light refracting bodies may have any composition and conformation. In one embodiment, the conformation of the light refracting bodies is a hollow sphere. In a further embodiment, the hollow sphere is filled with a substance having a refractive index which is different from the material from which the hollow sphere itself is made, yielding a structure which refracts UV radiation. In another embodiment, the composition of the light refracting bodies, specifically the material from which the hollow sphere itself is made, includes a styrene-acrylate copolymer composition. In a further embodiment, the composition of the light refracting bodies is a latex.

According to one particular embodiment of the invention, the light refracting bodies are constituted of a copolymer of styrene and (meth)acrylic acid or one of its alkyl esters under the INCI name Styrene/Acrylates Copolymer, such as the product sold under the tradename SUNSPHERES® powder by the company Dow chemical, which is an aqueous dispersion containing about 86% of Styrene/Acrylates Copolymer in a mixture of about 11% of PEG-8 Laurate, about 2.5% of water, and about 0.5% of Sodium Dodecylbenzenesulfonate.

In one embodiment, the SPF boosters suitable for use with the invention have a particle size which ranges generally from about 100 to about 380 nm, alternatively from about 150 to about 375 nm, alternatively from about 190 to about 350 nm, alternatively from about 251 to about 325 nm, the particle size being a volume-average particle size measured by a photon correlation spectrometer such as a Brookhaven BI-90 photon correlation spectrophotometer.

The light refracting bodies may possess any suitable void fraction, including, but not limited to, a void fraction of 0.1% to 50%, alternatively 5% to 50%. In some instances, the void fractions may be determined by comparing the volume occupied by the light refracting bodies after having been compacted from a diluted dispersion in a centrifuge, relative to the volume of non-void particles of the same composition.

Light refracting bodies which are hollow latex particles, according to one embodiment of the invention, are obtained from particles comprising at least one polymer for the core and at least one polymer for the shell. The core polymer and the shell polymer may be obtained from a single polymerization step or from a sequence of polymerization steps. Such hollow latex particles may be provided as part of an aqueous dispersion that is stabilized with at least one emulsifier.

The hollow latex particles may be prepared by any suitable method, including, but not limited to the conventional techniques of emulsion polymerization. Such processes are described especially in U.S. Pat. Nos. 4,427,836, 4,469,825, 4,594,363, 4,677,003, 4,920,160, and 4,970,241 or by the conventional techniques of polymerization that are described in the following patents and patent applications: EP267726, EP331421, U.S. Pat. No. 490,229, and U.S. Pat. No. 5,157,084. The above patents are incorporated by reference in their entirety.

The monomers used for the shell of the latex particles may include one or more unsaturated nonionic ethylenic units. Optionally one or more monoethylenically unsaturated monomers containing at least one carboxylic acid group may be polymerized in the shell. In one embodiment, the monomers constituting the shell are selected such that they exhibit a glass transition temperature (Tg) which is sufficiently high to withstand the void of the hollow latex particle. The glass transition temperature may be greater than 50° C., alternatively greater than 60° C., alternatively greater than 70° C. The glass temperature (Tg) may be determined by differential scanning calorimetry.

The monomers used in the emulsion polymerization for the core polymer of the hollow latex particles of the invention may include one or more monoethylenically unsaturated monomers containing at least one carboxylic acid group. The core may include at least 5% by weight of monoethylenically unsaturated monomers containing at least one carboxylic acid group, relative to the total weight of the core monomers. The core polymer may, for example, be obtained by emulsion homopolymerization of the monoethylenically unsaturated monomer containing at least one acid group or by copolymerization of two or three monoethylenically unsaturated monomers containing at least one acid group. In one embodiment, the monoethylenically unsaturated monomer containing at least one acid group is copolymerized with one or more ethylenically unsaturated nonionic monomers.

The core polymer or the shell polymer may contain from 0.1% to 20% by weight, and, in some embodiments, from 0.1% to 3% by weight, of polyethylenically unsaturated monomers, such as ethylene glycol di(meth)acrylate, allyl (meth)acrylate, 1,3-butanediol di(meth)acrylate, diethylene glycol di(meth)acrylate, trimethylolpropane tri(meth)acrylate, or divinylbenzene, relative to the total weight of the core monomers. Alternatively, the core polymer or the shell polymer may optionally contain from 0.1% to 60% by weight of butadiene, relative to the total weight of the core monomers.

The monoethylenically unsaturated monomers containing at least one carboxylic acid group may include, by way of example, acrylic acid, methacrylic acid, acryloyloxypropionic acid, (meth)acryloyloxypropionic acid, itaconic acid, aconitic acid, maleic acid or maleic anhydride, fumaric acid, crotonic acid, monomethyl maleate, monomethyl fumarate, and monomethyl itaconate.

In one embodiment, the monomer is selected from acrylic acid and methacrylic acid. The monoethylenically unsaturated nonionic monomers may include, by way of example, styrene, vinyl toluene, vinyl acetate, vinyl chloride, vinylidene chloride, acrylonitrile, (meth)acrylamide, $C1-C_{20}$ alkyl esters of (meth)acrylic acid, and $(C_3-C_{20})$ alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, and stearyl (meth)acrylate. As used herein, "(meth)acrylic" denotes the general expression encompassing both methacrylic or acrylic, and "(meth)acrylate" denotes the general expression encompassing both methacrylate or acrylate.

The void of the core of the latex particles may be produced by swelling the core with a swelling agent comprising one or more volatile compounds. The agent penetrates the shell in order to swell the core. The volatile components of the swelling agent may be subsequently removed by drying the latex particles, thus creating a void within the particles. The agent is, in some embodiments, an aqueous base. Mention may be made, for example, of ammonia, ammonium hydroxide, alkali metal hydroxides, such as sodium hydroxide, and volatile amines, such as trimethyl amine or triethylamine.

The hollow latex particles may be introduced into the composition with the swelling agent. In such an embodiment, the volatile compounds are removed when the composition is dried. The hollow latex particles may also be added to the composition after the volatile compounds of the swelling agent have been removed.

In one embodiment, the hollow latex particles are those described in patent U.S. Pat. No. 5,663,213 and patent application EP1092421, which are hereby incorporated by reference in their entirety.

In another embodiment, the hollow spheres of the light refracting bodies of the SPF booster include glass microspheres. Glass microspheres used in the compositions may be essentially homogeneous and essentially uniform in sphericity. The glass microspheres may have any suitable mean particle size, including, but not limited to, a mean particle size of between about 5 and 70 µm, alternatively from about 10 µm to 20 µm. Glass microspheres may include hollow microspheres of calcium aluminum borosilicate (commercially available from Presperse Inc. under the tradename LUXSIL®), sodium borosilicate particulates (commercially available from PQ Corporation under the tradename Q-CEL 570), and calcium sodium borosilicate hollow microspheres (commercially available from 3M under the tradenames ES 22 and 1K), calcium/sodium borosilicate microspheres (commercially available from 3M's under the tradename Scotchlite™ $K_{20}$ product).

In yet another embodiment, the light refracting bodies of the SPF booster include porous silica in the form of microparticles, in particular, spherical microparticles. The spherical microparticles of porous silica may have any suitable mean particle size, including, but not limited to, a mean particle size ranging from 0.5 µm to 20 µm, alternatively from 3 µm to 15 µm. Further, the microparticles may have any suitable specific surface, including, but not limited to, a specific surface ranging from 50 $m^2/g$ to 1,000 $m^2/g$, alternatively from 150 $m^2/g$ to 800 $m^2/g$. Also, the microparticles may have any suitable specific pore volume, including, but not limited to, a specific pore volume ranging from 0.5 ml/g to 5 ml/g, alternatively from 1 ml/g to 2 ml/g. By way of example, the porous silica spherical microparticles may include commercial products such as Silica Beads SB 150 from Myoshi, Sunsphere H-51 from Asahi Glass, Sunsil 130 from Sunjin, Spherica P-1500 from Ikeda Corporation, and Sylosphere from Fuji Silysia.

In one embodiment, the SPF booster includes at least one material selected from the group consisting of (co)polymers of (meth)acrylic acid, (meth)acrylates, and/or styrene, glass, and silica. In another embodiment, the SPF booster includes at least two materials selected from the group consisting of (co)polymers of (meth)acrylic acid, (meth)acrylates, and/or styrene, glass, and silica. In yet another embodiment, the SPF booster includes a (co)polymers of (meth)acrylic acid, (meth)acrylates, and/or styrene, glass, and silica. The (co)polymers of (meth)acrylic acid, (meth)acrylates, and/or styrene, may be made of poly(meth)acrylates, such as PMMA, a copolymer of (meth)acrylic acid and (meth)acrylates, and a copolymer of (meth)acrylic acid, (meth)acrylates, and styrene.

UV Filter

The composition may include any suitable amount of the at least one UV filter. In one embodiment, the composition includes about 15 wt % to about 35 wt % UV filter, alternatively about 20 wt % to about 30 wt %, alternatively about 25 wt %.

The at least one UV filter may include any suitable UV filter or UV filter system, including, but not limited to, solid organic lipsoluble UV filters, such as, but not limited to, butyl methoxydibenzoylmethane, and ethylhexyl trazone, liposoluble organic UV filters, such as, but not limited to, cinnamate compounds, anthranilates, salicylate compounds, dibenzoylmethane compounds, such as avobenzone, camphor compounds, β,β-diphénylacrylate compounds, triazine compounds, benzotriazole compounds, benzalmalonate compounds (particularly those cited in U.S. Pat. No. 5,624,663), imidazoline compounds, p-minobenzoate compounds (PABA), benzoxazole compounds (as described in patent applications EP0832642, EP1027883, EP1300137, and DE10162844), UV-filter polymers and UV-filter silicones (as described in patent application WO-93/04665), α-alkyl-styréne dimers (as described in patent application DE19855649), 4,4-diarylbutadiens (as described in patent applications EP0967200, DE19746654, DE19755649, EP-A-1008586, EP1133980, and EP133981), mérocyanine (as described in patents U.S. Pat. No. 4,195,999, WO2004/006878, WO2008/090066, WO2011113718, WO2009027258, and the documents IP COM JOURNAL No 000179675D published on Feb. 23 2009, IP COM JOURNAL No 000182396D published on Apr. 29, 2009, IP COM JOURNAL No 000189542D published on Nov. 12 2009, IP COM Journal No IPCOM000011179D published on Mar. 4, 2004), and their mixtures. The above documents are incorporated by reference in their entirety.

By way of non-limiting example, at least one UV filter or UV filter system may include (listed by INCI name): dibenzoylmethane compounds such as butylmethoxydibenzoylmethane (for example, as sold under the trade name Parsol 178® by DSM Nutritional Products, Inc.) and isopropyldibenzoylmethane; para-aminobenzoic compounds such as ethyl PABA, ethyl dihydroxypropyl PABA, ethylhexyl diméthyl PABA (sold under the name ESCALOL 507® by ISP), and glyceryl PABA; salicylic derivatives such as homosalate (sold under the commercial name Eusolex HMS by Rona/EM Industries) and ethylhexyl salicylate (sold under the commercial name NEO HELIOPAN OS by SYMRISE); cinnamic derivatives such as ethylhexyl methoxycinnamate (sold under the commercial name PARSOL MCX by DSM NUTRITIONAL PRODUCTS), isopropyl methoxy cinnamate, isoamyl methoxy cinnamate (sold under the commercial name NEO HELIOPAN E 1000 by SYMRISE), and cinoxate, diisopropyl methylcinnamate; derivatives of β,β-diphenylacrylate such as octocrylene (sold under the commercial name UVINUL N539 by BASF) and etocrylene (sold under the commercial name UVINUL N35 by BASF); and hexyl 2-(4-diethylamino-2-hydroxybenzoyl) benzoate (sold under the commercial name UVINUL A Plus or in the form of a mixture with octylmethoxycinnamate under the commercial name UVINUL A+B by BASF); benzylidenecamphor derivatives such as 3-Benzylidene camphor (manufactured under the commercial name MEXORYL SD by CHIMEX), 4-Methylbenzylidene camphor (sold under the commercial name EUSOLEX 6300 by MERC), and polyacrylamidomethyl benzylidene camphor (manufactured under the commercial name MEXORYL SW by CHIMEX); phenyl benzotriazole derivatives such as drometrizole trisiloxane (sold under the commercial name Silatrizole by RHODIA CHIMIE); triazine derivatives such as bis-ethylhexyloxyphenol methoxyphenyl triazine (sold under the commercial name TINOSORB S by BASF), ethylhexyl triazone (sold under the commercial name UVINUL T150 by BASF), diethylhexyl butamido triazone (sold under the commercial name UVASORB HEB by SIGMA 3V), 2,4,6-tris(4'-aminobenzalmalonate dinéopentyle)-s-triazine, 2,4,6-tris-(diisobutyle-4'-amino benzalmalonate)-s-triazine, and 2,4-bis (dinéopentyle-4'-aminobenzalmalonate)-6-(4'-aminobenzoate de n-butyle)-s-triazine; triazine silicones substituted by two aminobenzoates groups such 2,4-bis-(n-butyl 4'-aminobenzalmalonate)-6-[(3-{1,3,3,3-tetramethyl-1-[(trimethyl-silyloxy]disiloxanyl}propyl)amino]-s-triazine (and others as described in the patent EP0841341); anthranilic derivatives such as menthyl anthranilate (sold under the commercial name NEO HELIOPAN MA by SYMRISE), imidazoline derivatives such as ethylhexyl di methoxybenzylidene dioxoimidazoline propionate; benzalmalonate derivatives such as dineopentyl 4'-methoxybenzalmalonate and polyorganosiloxane with benzalmalonate functions such as Polysilicone-15 (sold under the commercial name PARSOL SLX by DSM NUTRITIONAL PRODUCTS); derivatives of 4,4-diarylbutadiene such as 1,1-dicarboxy (2,2'-diméthyl-propyl)-4,4-diphénylbutadiene; benzoxazole derivatives such as 2,4-bis-[5-1(diméthylpropyl)benzoxazol-2-yl-(4-phenyl)-imino]-6-(2-ethyhexyl)-imino-1,3,5-triazine (sold under the commercial name Uvasorb K2A by Sigma 3V); lipophilic merocyanine derivatives such as Octyl-5-N,N-diethylamino-2-phenysulfonyl-2,4-pentadienoate; terephthalylidene dicamphor sulfonic acid (Sold under the commercial name Mexoryl SX by CHIMEX; and drometrizole trisiloxane (Sold under the commercial name Mexoryl XL by RHODIA).

In one embodiment, the at least one UV-A filter is avobenzone and at least one UV-B filter includes, consists essentially of or consists of octisalate, octocrylene, and homosalate. In another embodiment, the UV-A filter is avobenzone and the UV-B filter includes, consists essentially of or consists of at least two of octisalate, octocrylene, and homosalate. In still another embodiment, the UV filter system including the UV-A and the UV-B filters includes, consists essentially of or consists of each of avobenzone, octisalate, octocrylene, and homosalate.

Further Ingredients

In addition to the at least one photostabilizer having anti-oxidant properties, the at least one SPF booster, and the at least one UV-A and one UV-B filter, which may be considered to be the essential ingredients of the composition, the composition may further include other ingredients for forming the emulsion, as well as to modify the aesthetics (including scent, visual appearance and feel) and other properties of the composition. Such other ingredients may include, but are not limited to, water, EDTA, preservatives, emulsifiers, thickeners, humectants, emollients, aesthetic modifiers, film formers, anti-oxidants, TEA, denatured alcohols, perfumes, pigments, and whatever additions may be beneficial or particular to the desired form of the compositions or final product.

Optional Powders

The composition may optionally include powders. The optional powders provide formulas that are smoother and softer on the skin. Representative powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesiumstearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative powder includes, for example, polymethylsilsesquioxane. Powders may be present in the compositions in amounts generally ranging from about 0.1% to about 5% by weight or about 0.1% to about 10% by weight, based on the total weight of the composition.

Combination of Photostabilizer and SPF Booster

An unexpected synergistic effect has been discovered arising from the combination of the at least one photostabilizer and the at least one SPF booster. The synergistic effect may be achieved when there is a sufficient concentration of each of the least one photostabilizer and the at least one SPF booster in the composition as well as ratio of the least one photostabilizer and the at least one SPF booster which is within a suitable range.

The composition may include any suitable amount of the at least one photostabilizer and the at least one SPF booster. In one embodiment, the composition includes at least 2 wt % combined of the at least one photostabilizer and the at least one SPF booster, alternatively at least 3 wt %, alternatively at least 4 wt %, alternatively at least 5 wt %, alternatively between 1.5 wt % to about 14 wt %, alternatively between about 1.5 wt % to about 5 wt %, alternatively between about 5 wt % to about 9 wt %, alternatively between about 9 wt % to about 14 wt %.

In one embodiment, the composition include at least 0.5 wt % of the at least one photostabilizer, alternatively at least 1 wt %, alternatively at least 1.5 wt %, alternatively at least 2 wt %, alternatively between about 0.5 wt % to about 7 wt %, alternatively between about 1 wt % to about 5 wt %.

In another embodiment, the composition includes at least 1 wt % of the at least one SPF booster, alternatively at least 1.5 wt %, alternatively at least 2 wt %, alternatively at least 2.5 wt %, alternatively between about 1 wt % to about 7 wt %, alternatively between about 2 wt % to about 5 wt %.

The ratio of the at least one photostabilizer to the at least one SPF booster may be any suitable ratio, including, but not limited to, a ratio between about 1:14 to about 7:1, alternatively between about 1:7 to about 5:1, alternatively between about 1:4 to about 4:1, alternatively between about 1:2 to about 2:1.

SPF and UV-A and UV-B

UV-Filters, active in UV-A and/or UV-B regions, used for the present invention can be water-soluble, fat-soluble or insoluble in commonly used cosmetic solvents. UV-A filter comprise groups of compounds which absorb light predominantly in the range of wavelengths 400 nm to 320 nm (UV-A) and UV-B filter comprise groups of compounds which absorb light predominantly in the range of wavelengths 400 nm to 320 nm 320 nm to 280 nm (UV-B). The composition may include a sun protection factor (SPF) of at least about 30, alternatively at least about 35, alternatively at least about 40, alternatively at least about 45, alternatively at least about 50, alternatively at least about 55, alternatively at least about 60 or higher. Independently, the composition may include a UV-A of at least about 15, alternatively at least about 20, alternatively at least about 25, alternatively at least about 30, alternatively at least about 35, alternatively at least about 40, alternatively at least about 45 or higher. In one embodiment, the composition includes an SPF of at least about 30 and a UV-A of at least about 15, alternatively an SPF of at least about 35 and a UV-A of at least about 20, alternatively an SPF of at least about 40 and a UV-A of at least about 25, alternatively an SPF of at least about 45 and a UV-A of at least about 30, alternatively an SPF of at least about 50 and a UV-A of at least about 35, alternatively an SPF of at least about 55 and a UV-A of at least about 40, alternatively an SPF of at least about 60 or higher and a UV-A of at least about 45 or higher. According to an embodiment of the invention, U V-A and UV-B can be two separate UV filters or they can be one UV filter with both UV-A and UV-B sun protection factor.

Composition

The composition may be any suitable composition, including, but not limited to, a skincare composition, a hair care composition, a sunscreen composition, a skin-tanning composition, a cosmetic composition, a make-up composition, a lip balm, a skin facial peeling composition, a moisturizing composition, an anti-aging skincare composition, or a combination thereof.

EXAMPLES

The method of making each of the examples provided in Tables 1, 2, 3, 4, 5, and 6 is generally the same.

TABLE 1

Oil in Water Emulsion:

| Phase | Ingredients | Comparative Ex. 1 | Ex. 1 |
|---|---|---|---|
| A | water | Q.S | Q.S |
| | EDTA | 0.10 | 0.10 |
| | preservative | 1.30 | 1.30 |
| | emulsifiers | 2.99 | 2.99 |
| | thickener | 2.20 | 2.20 |
| | humectant | 1.40 | 1.40 |
| B | emollient | 3.00 | 3.00 |
| | avobenzone | 3.00 | 3.00 |
| | oxybenzone | 3.86 | — |
| | octocrylene | 6.00 | 7.00 |
| | ethylhexyl salicylate | 3.21 | 5.00 |
| | homosalate | 10.72 | 10.00 |
| | aesthetic modifiers | 7.00 | 7.00 |
| | diethylhexyl syringylidenemalonate | 0.10 | 1.00 |
| B1 | styrene/acrylates copolymer | 4.00 | 4.00 |
| C | film former | 2.28 | 2.28 |
| D | anti-oxidants | 0.35 | 0.35 |
| E | water | 0.50 | 0.50 |
| | tea | 0.25 | 0.25 |
| F | denatured alcohol | 2.00 | 2.00 |
| Properties | | | |
| % UV Filters | | 26.79 | 25.00 |
| SPF (in-vivo) | | 68.9 | 75.25 |
| UV-A (in-vivo) | | 26.72 | 28.00 |
| | Critical Wavelength | 377.67 | 378 |

In Table 1, an inventive example of the composition is shown in comparison to a non-inventive example having a higher content of UV filter as well as having 3.86 wt % oxybenzone, which is a UV-A filter, not only has a higher SPF rating, but also has a high UV-A rating. Thus, due to the surprising synergistic relationship between the photostabilizer and the SPF booster, improved UV-A and SPF performance is achieved in the composition even lacking oxybenzone.

TABLE 2

Water in Oil Emulsion:

| INCI Name/Ingredients | Comparative Ex. 2 | Ex. 2 |
|---|---|---|
| disodium EDTA | 0.1 | 0.1 |
| sodium chloride | 0.5 | 0.5 |
| Preservative | 1.3 | 1.3 |
| diethylhexyl syringylidenemalonate | 3 | 1 |
| Emollients | 5 | 5 |
| Thickener | 1.2 | 1.2 |
| styrene/acrylates copolymer | 4 | 4 |
| Silicone | 13 | 13 |

TABLE 2-continued

Water in Oil Emulsion:

| INCI Name/Ingredients | Comparative Ex. 2 | Ex. 2 |
|---|---|---|
| Emulsifier | 3.42 | 3.42 |
| Alcohol | 7 | 7 |
| Water | Q.S | Q.S. |
| benzophenone-3 (oxybenzone) | 3.86 | — |
| butyl methoxydibenzoylmethane | 3 | 3 |
| ethylhexyl salicylate | 3.21 | 5 |
| Octocrylene | 6 | 7 |
| Homosalate | 10.72 | 10 |
| cassia alata leaf extract | 0.17 | 0.17 |
| Properties | | |
| % UV Filters | 26.79 | 25 |
| SPF (in-vivo) | 72 | 67 |
| UV-A (in-vivo) | 68 | 74 |
| Critical Wavelength | 376 | 377 |

In Table 2, an inventive example of the composition is shown in comparison to a non-inventive example having a higher content of UV filter and a higher photostabilizer content, as well as having 3.86 wt % oxybenzone, which is a UV-A filter, exhibiting only a small reduction in SPF rating, but nonetheless actually having an increase in the UV-A rating. Thus, due to the surprising synergistic relationship between the photostabilizer and the SPF booster, improved UV-A performance is achieved in the composition having less photostabilizer and lacking oxybenzone.

TABLE 3

| Phase | INCI Names/Ingredients | Ex. 3 | Ex. 4 | Ex. 5 | Ex. 6 |
|---|---|---|---|---|---|
| A | Water | 51.63 | 46.63 | 46.63 | 46.63 |
|   | disodium EDTA | 0.10 | 0.10 | 0.10 | 0.10 |
|   | preservative | 1.30 | 1.30 | 1.30 | 1.30 |
|   | emulsifiers | 2.70 | 2.70 | 2.70 | 2.70 |
|   | polymeric emulsifier/stabilizer | 0.29 | 0.29 | 0.29 | 0.29 |
|   | thickener | 2.20 | 2.20 | 2.20 | 2.20 |
|   | humectant | 1.40 | 1.40 | 1.40 | 1.40 |
| B | emollient | 3.00 | 3.00 | 3.00 | 3.00 |
|   | avobenzone | 3.00 | 3.00 | 3.00 | 3.00 |
|   | oxybenzone | 0.00 | 0.00 | 0.00 | 0.00 |
|   | octocrylene | 7.00 | 7.00 | 7.00 | 7.00 |
|   | ethylhexyl salicylate | 5.00 | 5.00 | 5.00 | 5.00 |
|   | homosalate | 10.00 | 10.00 | 10.00 | 10.00 |
|   | diethylhexyl syringylidenemalonate | 0.00 | 0.00 | 5.00 | 1.00 |
|   | aesthetic modifiers | 7.00 | 7.00 | 7.00 | 7.00 |
| B1 | styrene/acrylates copolymer | 0.00 | 5.00 | 0.00 | 4.00 |
| C | film former | 2.28 | 2.28 | 2.28 | 2.28 |
| D | anti-oxidants | 0.35 | 0.35 | 0.35 | 0.35 |
| E | Water | 0.50 | 0.50 | 0.50 | 0.50 |
|   | Tea | 0.25 | 0.25 | 0.25 | 0.25 |
| F | denatured alcohol | 2.00 | 2.00 | 2.00 | 2.00 |
| % UV Filters | | 25.00 | 25.00 | 25.00 | 25.00 |
| Properties | | | | | |
| SPF (in-vitro) | | 43.00 | 70.00 | 42.00 | 101.00 |
| UV-A (in-vitro) | | 22.00 | 35.00 | 27.00 | 52.00 |

In Table 3, an inventive example of the composition is shown in comparison to non-inventive examples lacking at least one of the photostabilizer and the SPF booster, wherein all compared formulas include the same UV filters and the same amount of each UV filter, demonstrating dramatic increases in both the SPF rating and the UV-A rating, and clearly showing the unexpected synergy between the photostabilizer and the SPF booster in the inventive composition.

TABLE 4

Oil in Water Semitransparent Emulsion:

| INCI US/Ingredients | Ex. 7 |
|---|---|
| disodium EDTA | 0.1 |
| preservative | 1.4 |
| plasticizer | 0.06 |
| diethylhexyl syringylidenemalonate | 2 |
| hydrocarbon | 5 |
| film former | 2.79 |
| styrene/acrylates copolymer | 4 |
| Silicone | 8.5 |
| Water | Q.S. |
| avobenzone | 3 |
| octisalate | 5 |
| octocrylene | 7 |
| homosalate | 10 |
| emulsifier | 4.25 |
| cassia alata leaf extract | 0.1 |
| tocopherol | 0.1 |
| Properties | |
| SPF (in-vivo) | 73 |
| UV-A (in-vivo) | 27.6 |

In Table 4, an inventive example of the composition is shown demonstrating high SPF and UV-A performance.

TABLE 5

| | Formula | Comparative Ex. 1 | Ex. 3 | Ex. 4 | Ex. 5 | Ex. 6 |
|---|---|---|---|---|---|---|
| UV filters | avobenzone | 3 | 3 | 3 | 3 | 3 |
|   | octocrylene | 6 | 7 | 7 | 7 | 7 |
|   | octisalate | 3.21 | 5 | 5 | 5 | 5 |
|   | homosalate | 10.72 | 10 | 10 | 10 | 10 |
|   | oxybenzone | 3.86 | 0 | 0 | 0 | 0 |
| Total UV fillers | | 26.79 | 25.00 | 25.00 | 25.00 | 25.00 |
| SPF boosters | styrene/acrylate copolymer | 4 | 0 | 5 | 0 | 4 |
| Photostabilizer/AntiOxidant | diethylhexyl syringylidene-malonate | 0.1 | 0 | 0 | 5 | 1 |

TABLE 5-continued

| Formula | Comparative Ex. 1 | Ex. 3 | Ex. 4 | Ex. 5 | Ex. 6 |
|---|---|---|---|---|---|
| Efficacy Results | | | | | |
| SPF (in-vitro) | 106.56 | 43.43 | 69.65 | 41.78 | 101.34 |
| UV-A (In-vitro) | 56.74 | 22.28 | 35 | 27.3 | 52.04 |

In Table 5, an inventive example of the composition is shown in comparison to a non-inventive example having oxybenzone and non-inventive examples lacking at least one of the photostabilizer and the SPF booster, demonstrating that the SPF and UV-A ratings of the composition having the synergistic combination of photostabilizer and UV booster nearly equal the efficacy of the non-inventive example having oxybenzone, whereas the non-inventive examples lacking the synergistic combination of photostabilizer and UV booster evidences substantial reductions in both SPF and UV-A ratings.

TABLE 6

| Phase | Ingredients | Ex. 3 | Ex. 4 | Ex. 5 | Ex. 7 | Ex. 8 | Ex. 9 | Ex. 10 | Ex. 11 |
|---|---|---|---|---|---|---|---|---|---|
| A | water | 51.63 | 46.63 | 46.63 | 46.63 | 46.63 | 46.63 | 46.63 | 46.63 |
| | disodium EDTA | 0.10 | 0.10 | 0.10 | 0.10 | 0.10 | 0.10 | 0.10 | 0.10 |
| | preservative | 1.30 | 1.30 | 1.30 | 1.30 | 1.30 | 1.30 | 1.30 | 1.30 |
| | emulsifiers | 2.70 | 2.70 | 2.70 | 2.70 | 2.70 | 2.70 | 2.70 | 2.70 |
| | polymeric emusifier/ stabilizer | 0.29 | 0.29 | 0.29 | 0.29 | 0.29 | 0.29 | 0.29 | 0.29 |
| | thickener | 2.20 | 2.20 | 2.20 | 2.20 | 2.20 | 2.20 | 2.20 | 2.20 |
| | Humectant | 1.40 | 1.40 | 1.40 | 1.40 | 1.40 | 1.40 | 1.40 | 1.40 |
| B | Emollient | 3.00 | 3.00 | 3.00 | 3.00 | 3.00 | 3.00 | 3.00 | 3.00 |
| | avobenzone | 3.00 | 3.00 | 3.00 | 3.00 | 3.00 | 3.00 | 3.00 | 3.00 |
| | oxybenzone | 0.00 | 0.00 | 0.00 | 0.00 | 0.00 | 0.00 | 0.00 | 0.00 |
| | octocrylene | 7.00 | 7.00 | 7.00 | 7.00 | 7.00 | 7.00 | 7.00 | 7.00 |
| | ethylhexyl salicylate | 5.00 | 5.00 | 5.00 | 5.00 | 5.00 | 5.00 | 5.00 | 5.00 |
| | homosalate | 10.00 | 10.00 | 10.00 | 10.00 | 10.00 | 10.00 | 10.00 | 10.00 |
| | diethylhexyl syringylidene-malonate | 0.00 | 0.00 | 5.00 | 2.00 | 3.00 | 4.00 | 1.00 | 1.00 |
| | aesthetic modifiers | 7.00 | 7.00 | 7.00 | 7.00 | 7.00 | 7.00 | 7.00 | 7.00 |
| B1 | styrene/ acrylates copolymer | 0.00 | 5.00 | 0.00 | 3.00 | 2.00 | 1.00 | 1.00 | 4.00 |
| C | film former | 2.28 | 2.28 | 2.28 | 2.28 | 2.28 | 2.28 | 2.28 | 2.28 |
| D | anti-oxidants | 0.35 | 0.35 | 0.35 | 0.35 | 0.35 | 0.35 | 0.35 | 0.35 |
| E | Water | 0.50 | 0.50 | 0.50 | 0.50 | 0.50 | 0.50 | 0.50 | 0.50 |
| | TEA | 0.25 | 0.25 | 0.25 | 0.25 | 0.25 | 0.25 | 0.25 | 0.25 |
| F | denatured alcohol | 2.00 | 2.00 | 2.00 | 2.00 | 2.00 | 2.00 | 2.00 | 2.00 |
| Properties | | | | | | | | | |
| % UV Filters | | 25.00 | 25.00 | 25.00 | 25.00 | 25.00 | 25.00 | 25.00 | 25.00 |
| SPF (in-vitro) | | 43.00 | 70.00 | 42.00 | 83.00 | 96.00 | 85.00 | 62.00 | 101.00 |
| UV-A (in-vitro) | | 22.00 | 35.00 | 27.00 | 44.00 | 53.00 | 49.00 | 33.00 | 52.00 |

In Table 6, five inventive examples of the composition are shown in comparison to three non-inventive examples lacking at least one of the photostabilizer and the SPF booster, wherein all compared formulas include the same UV filters and the same amount of each UV filter. The inventive examples demonstrate generally dramatic increases in both the SPF rating and the UV-A rating, clearly showing the unexpected synergy between the photostabilizer and the SPF booster in the inventive composition, although one inventive example having the least amount of SPF booster and photostabilizer does show merely comparable SPF and UV-A ratings to a non-inventive example having a large amount of SPF booster.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A photostable UV-A/UV-B sunscreen composition comprising:
   a diethylhexyl syringylidenemalonate photostabilizer present in an amount of about 1 weight percent to about 4 weight percent based on the total weight of the composition;

a styrene/acrylates copolymer composition SPF booster present in an amount of about 1 weight percent to about 4 weight percent based on the total weight of the composition; and at least a UV-filter system consisting of avobenzone, octisalate, octocrylene and Homosalate;

wherein the weight ratio of the styrene/acrylates copolymer composition SPF booster to the diethylhexyl syringylidenemalonate photostabilizer is 3:2 to 4:1;

wherein the avobenzone is present in an amount of 3 weight percent, the octisalate is present in an amount of 5 weight percent, the octocrylene is present in an amount of 7 weight percent, and the Homosalate is present in the amount of 10 weight percent.

2. A photostable UV-A/UV-B sunscreen composition comprising:

a diethylhexyl syringylidenemalonate photostabilizer present in an amount of about 1 weight percent to about 2 weight percent based on the total weight of the composition;

a styrene/acrylates copolymer composition SPF booster present in an amount of about 3 weight percent to about 4 weight percent based on the total weight of the composition; and at least a UV-filter system consisting of avobenzone, octisalate, octocrylene and Homosalate;

wherein the weight ratio of the styrene/acrylates copolymer composition SPF booster to the diethylhexyl syringylidenemalonate photostabilizer is 3:2 to 4:1;

wherein the avobenzone is present in an amount of 3 weight percent, the octisalate is present in an amount of 5 weight percent, the octocrylene is present in an amount of 7 weight percent, and the Homosalate is present in the amount of 10 weight percent.

* * * * *